US012097327B2

(12) United States Patent
Murray

(10) Patent No.: US 12,097,327 B2
(45) **Date of Patent: *Sep. 24, 2024**

(54) EMERGENCY RESPIRATORY SUPPORT DEVICES, SYSTEMS, AND METHODS

(71) Applicant: Cowboy EMS, LLC, Newton, NC (US)

(72) Inventor: David Murray, Newton, NC (US)

(73) Assignee: Cowboy EMS, LLC, Newton, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,206

(22) Filed: Mar. 28, 2022

(65) Prior Publication Data

US 2022/0395664 A1 Dec. 15, 2022

Related U.S. Application Data

(63) Continuation of application No. 16/465,185, filed as application No. PCT/US2018/012163 on Jan. 3, 2018, now Pat. No. 11,285,288.

(Continued)

(51) Int. Cl.
*A61M 16/06* (2006.01)
*A61G 13/12* (2006.01)

(Continued)

(52) U.S. Cl.
CPC ..... *A61M 16/0683* (2013.01); *A61G 13/1215* (2013.01); *A61M 16/0084* (2014.02); *A61M 16/125* (2014.02); *A61M 2202/0208* (2013.01)

(58) Field of Classification Search
CPC .......... A61M 16/0084; A61M 16/0488; A61M 16/06; A61M 16/0683; A61M 16/125;

(Continued)

(56) References Cited

U.S. PATENT DOCUMENTS 3,330,274 A * 7/1967 Ray ...................... A62B 18/025 128/206.26
3,461,858 A * 8/1969 Michelson ........... A61H 31/008 206/572

(Continued)

FOREIGN PATENT DOCUMENTS

WO WO 2018/129024 7/2018

OTHER PUBLICATIONS

International Preliminary Report on Patentability (Chapter 1 of the Patent Cooperation Treaty) corresponding to International application No. PCT/US2018/012163 dated Jul. 9, 2019.

(Continued)

*Primary Examiner* — Colin W Stuart
*Assistant Examiner* — Douglas Y Sul
(74) *Attorney, Agent, or Firm* — KDW Firm PLLC

(57) ABSTRACT

Devices, systems, and/or methods for immobilizing a patient's head and simultaneously providing emergency respiration for the patient includes, in some embodiments, a head immobilizer, a bag valve mask (BVM), an endotracheal tube (ET) bracket, and/or an oxygen face mask. In some embodiments where head immobilization is not needed, a cardiopulmonary resuscitation (CPR) board may be used in lieu of the head immobilizer. Each such embodiment is configured to require reduced manual intervention by a caregiver without reducing the effectiveness of each medical device and/or system. An adjustable BVM holder integrated into the head immobilizer secures the BVM on the patient. In embodiments with a BVM, only a single hand is necessary to provide emergency respiration, freeing the caregiver's other hand for other caregiving tasks. Such a head immobilizer may secure an ET bracket and/or face mask to a patient, allowing for hands-free operation during patient treatment, movement, and transportation.

17 Claims, 12 Drawing Sheets

Related U.S. Application Data

(60) Provisional application No. 62/441,722, filed on Jan. 3, 2017.

(51) Int. Cl.
*A61M 16/00* (2006.01)
*A61M 16/12* (2006.01)

(58) Field of Classification Search
CPC ........ A62B 9/04; A61G 13/1215; A61G 7/07; A61G 7/072; A62F 5/05883; A62F 5/05891; A62F 5/3707
See application file for complete search history.

(56) References Cited

U.S. PATENT DOCUMENTS 3,511,275 A 5/1970 Hewson
4,196,725 A * 4/1980 Gunderson ........... A61M 16/00 128/205.25
4,297,999 A * 11/1981 Kitrell ............... A61M 16/0084 128/205.16
5,154,186 A 10/1992 Laurin et al.
5,207,716 A 5/1993 McReynolds et al.
5,479,921 A 1/1996 Reif
5,711,295 A * 1/1998 Harris, II .......... A61M 16/0084 128/202.28
6,981,503 B1 * 1/2006 Shapiro ............. A61M 16/0683 128/845
7,124,757 B2 * 10/2006 Frank ................ A61M 16/0816 128/869
7,628,154 B2 12/2009 Bierman et al.
11,285,288 B2 * 3/2022 Murray .............. A61G 13/1215
2003/0131854 A1 7/2003 Kiefer et al.
2005/0241068 A1 * 11/2005 Tomcany ................ A61G 1/04 5/628
2005/0284472 A1 12/2005 Lin
2011/0036355 A1 2/2011 Farnum
2012/0013400 A1 1/2012 Chang et al.
2012/0145151 A1 * 6/2012 Bergman .......... A61M 16/0084 128/205.16
2013/0068233 A1 * 3/2013 De Lulio .......... A61M 16/0497 128/207.17
2019/0366027 A1 12/2019 Murray

OTHER PUBLICATIONS

International Search Report corresponding to International Application No. PCT/US2018/012163 12163 dated Apr. 5, 2018.
Notice of Publication corresponding to U.S. Appl. No. 16/465,185 dated Dec. 5, 2019.
Written Opinion of the International Searching Authority corresponding to International application No. PCT/US2018/012163 dated Apr. 5, 2018.
Office Action (Restriction Requirement) corresponding to U.S. Appl. No. 16/465,185 dated Jul. 30, 2021.
Notice of Allowance corresponding to U.S. Appl. No. 16/465,185 dated Jan. 25, 2022.

* cited by examiner 344
330
346
332
342
334
336
340
338
344

EMERGENCY RESPIRATORY SUPPORT DEVICES, SYSTEMS, AND METHODS

CROSS-REFERENCE TO RELATED APPLICATIONS

This application is a continuation of U.S. patent application Ser. No. 16/465,185 filed May 30, 2019, which is a national stage application under 35 U.S.C. § 371 of PCT Patent Application No. PCT/US2018/012163 filed Jan. 3, 2018, which claims the benefit of U.S. Provisional Patent Application Ser. No. 62/441,722 filed Jan. 3, 2017, the disclosures of each of which are incorporated herein by reference in their entireties.

TECHNICAL FIELD

The subject matter disclosed herein relates generally to the design and operation of emergency medical devices, systems, and methods of operating such devices and systems. More particularly, the subject matter disclosed herein relates to emergency respiration devices, systems, and methods of using such emergency respiration devices requiring less manual dexterity by medical caregivers during use on a patient.

BACKGROUND

The use of emergency respiratory devices and systems has rapidly become the standard of care for patients who require respiratory support. However, traditional respiratory support devices and systems require the use of at least one hand of an emergency caregiver, if not both hands. Typically, a mask must be secured over the face of the patient with at least one hand of the medical caregiver. Depending on the kind of supportive respiratory care being administered, both hands of the medical caregiver must, in some instances, be engaged with the emergency respiration equipment. For example, it is common for first responders (e.g., emergency medical technicians, or EMTs) to initially provide respiratory support with a bag valve mask (BVM) device. Current procedures call for a BVM device to be held in place by the hands of one or two medical caregivers at all times. The patient's head is held steady manually and at least one hand of the medical caregiver is used to hold the mask in place without breaking the seal around the mouth and nose of the patient. As such, when there is only one caregiver available to provide respiratory support to a patient with a BVM device, the caregiver is unable to undertake any other activities requiring manual dexterity, such as recording notes, calling for further support personnel via a communications device, or performing further diagnostic actions with his/her hands.

The same disadvantage is present when the mask is replaced by an endotracheal tube such as would be inserted into the trachea of the patient during an intubation procedure. While the need for persistent manual intervention by a caregiver is alleviated to a certain degree when the bag is replaced by a supplemental oxygen supply, it is still necessary for a caregiver to secure the mask or endotracheal tube in place (e.g., with a bracket) in such instances. This is especially difficult when the patient is suspected of having a spinal or cervical injury requiring head immobilization. In such instances, it is inadvisable to maneuver the patient any more than is absolutely necessary to stabilize and immobilize the patient, thus the safest course of action is to manually hold the mask over the mouth and nose of the patient while respiratory support is provided.

Accordingly, a need exists for emergency respiratory support devices, systems, and methods of providing respiratory support requiring less ongoing manual intervention and, in some cases, no ongoing manual intervention.

SUMMARY

The presently disclosed subject matter allows a clinician or medical personnel (e.g., a medical caregiver) to provide emergency respiratory support (e.g., oxygen or ambient air) without having to continually stabilize the patient's head and manually hold the oxygen mask to the face to achieve a consistent seal. The presently disclosed subject matter allows silicone-type masks, endotracheal tube (ET) brackets, and/or oxygen face masks to properly be held in place and to have an effective seal without wrapping straps around a patient's head or having to move the patient's head to apply head straps.

The emergency respiratory support devices and systems disclosed herein use a modified head immobilizer configured to immobilize the patient's head, securely hold the mask in place using a hook and loop system combined with straps to provide a consistent and substantially unbroken seal, and support and secure a respiratory support bag (e.g., as used in a BVM device) in place for timely ventilations of the patient. These devices and systems allow, in some embodiments, a clinician or medical provider to use their hands for other patient care needs between ventilations. The secured BVM mask can also, in some embodiments, assist in immobilizing the chin area of the patient's head. In embodiments where a full face silicone-type mask with multi-positioning cushioned forehead pad is used, the respiratory support system can assist in immobilizing the forehead of the patient as well. Indications, contraindications, and the use of air adjunct devices are the same with the emergency respiratory support devices and systems disclosed herein as with other BVM applications.

When using an ET bracket with the hands-free emergency respiratory support system disclosed herein, the conventional strap system that wraps around the patient's head may be replaced by one or more (e.g. two) hook and loop straps that attach securely to the sides of the head immobilizer. This embodiment allows a medical caregiver to apply the ET tube holder without having to move the patient's head for application. This method reduces the risk of causing further traumatic damage to a trauma patient. The head immobilizer can also be used to hold a patient's head in place and secure the bag and valve in a static position (e.g., connected to the endotracheal tube) so that medical caregiver(s) can provide other patient care procedures between each ventilation.

In some further embodiments, the silicone-type mask can be held in place with a strap fastened (e.g., using hook and loop material) to both sides of the head immobilizer. An improved mask seal can be provided over and around the nose and mouth of the patient and the mask can also be applied without having to remove the patient's head from the immobilization supports or raising the patient's head to apply the head strap. The secured mask can, in some embodiments, also assist in immobilizing the chin area.

In a first example embodiment, an emergency respiratory support system for providing respiratory support to a patient is disclosed, the system comprising: a base; a plurality of blocks arranged on opposite sides of a head of the patient; an assisted respiration device comprising a valve configured to provide ventilation and/or respiratory support to the patient; a holder assembly configured for attachment to the base and to secure the assisted respiration device relative to the patient; and one or more straps configured for attachment, at a first end, to a first of the plurality of blocks and, at a second end, to a second of the plurality of blocks, and to secure the assisted respiration device to the patient.

According to one aspect of this first example embodiment, one or more of the plurality of blocks has a vertically-oriented hole formed through a thickness thereof, the hole being configured to receive a retention tube, and the retention tube being configured to receive a first end of a support rod of the holder assembly inserted therein. According to a further aspect, the assisted respiration device comprises a bag configured to provide an air supply to the patient. In still another aspect, the air supply comprises a supplemental amount of oxygen from an external source, so an oxygen content of the air supply is elevated relative to an oxygen content of an ambient air source. In another aspect, the holder assembly further comprises: a support collar attached to the support rod at a second end thereof; a rotary support arm comprising a longitudinal channel formed through a thickness thereof; a first fastener configured to apply a compressive force to prevent a rotary movement of the rotary support arm around a longitudinal axis of the support rod; a sliding plate configured to move along, and be fixed at a plurality of positions along, the longitudinal channel; a second fastener configured to apply a compressive force to prevent a displacement of the sliding plate along a length of the channel; a support bar pivotably attached to the sliding plate; and a saddle configured to support the bag of the assisted respiration device, wherein the rotary support arm is configured to be fixed by the first fastener at a plurality of positions, relative to the support rod, along the length of the longitudinal channel. In yet another aspect, the assisted respiration device comprises a mask configured to cover a mouth and/or nose of the patient, and wherein the valve is configured to connect to an inlet of the mask. In a further aspect, the holder assembly is configured to maintain a substantially air-tight seal around the patient's mouth, without requiring the mask to be held in place by a hand of a medical caregiver. In an aspect of this embodiment, the mask is secured to the plurality of blocks by at least one of the one or more straps. In another aspect, the one or more straps comprise a first strap, which is configured to secure the mask over the nose and mask of the patient and also to secure a lower portion of the head of the patient in place, and a second strap, which is connected to the mask and is secured to a forehead of the patient. In still another aspect, the assisted respiration device comprises an endotracheal tube (ET) bracket that is configured to be secured to an endotracheal tube inserted in a trachea of the patient, and wherein the valve is configured to connect to an external end of the endotracheal tube. In another aspect, the bracket comprises a cushion configured to hold the bag. In yet another aspect, the system comprises an oxygen mask configured to receive a supply of oxygen from an external oxygen source. According to this embodiment, the oxygen mask can comprise a ring with a hook or loop fastener to secure the mask to a face of the patient using at least one of the one or more straps.

In a second example embodiment, a method of providing emergency respiratory support to a patient is disclosed, the method comprising: securing the patient to a base; providing an emergency respiratory support system comprising at least a valve and a bag; securing the respiratory support system to a holder assembly attached to the base using one or more straps; and supplying respiratory support to the patient using the emergency respiratory support system.

According to one aspect of this second example embodiment, the step of supplying respiratory support comprises supplying supplemental oxygen to the patient from an external oxygen source. According to another aspect of this second example embodiment, the emergency respiratory support system comprises an endotracheal tube and/or a mask secured to the patient by the holder assembly. In some further such embodiments, the mask is an oxygen mask. According to still another aspect of this second embodiment, the holder assembly comprises: a support collar attached to the support rod at a second end thereof; a rotary support arm comprising a longitudinal channel formed through a thickness thereof; a first fastener configured to apply a compressive force to prevent a rotary movement of the rotary support arm around a longitudinal axis of the support rod; a sliding plate configured to move along, and be fixed at a plurality of positions along, the longitudinal channel; a second fastener configured to apply a compressive force to prevent a displacement of the sliding plate along a length of the channel; a support bar pivotably attached to the sliding plate; and a saddle configured to support the bag of the assisted respiration device, wherein the rotary support arm is configured to be fixed by the first fastener at a plurality of positions, relative to the support rod, along the length of the longitudinal channel. According to another aspect of this second embodiment, the base is a head immobilizer structure. According to yet another aspect of this second embodiment, the step of supplying respiratory support to the patient is accomplished without manual intervention from a medical caregiver.

In a third example embodiment, an emergency respiratory support system for providing respiratory support to a patient is disclosed, the system comprising: a base; a plurality of blocks arranged on opposite sides of a head of the patient, wherein one or more of the plurality of blocks has a vertically-oriented hole formed through a thickness thereof, the hole being configured to receive a retention tube, and the retention tube being configured to receive a first end of a support rod of the holder assembly inserted therein; an assisted respiration device comprising a bag configured to provide an air supply to the patient, a mask configured to cover a mouth and/or nose of the patient, and a valve connected to an inlet of the mask and configured to regulate a flow of the air supply between the bag and the mask; a holder assembly configured for attachment to the base and to secure the assisted respiration device relative to the patient, the holder assembly comprising: a support collar attached to the support rod at a second end thereof; a rotary support arm comprising a longitudinal channel formed through a thickness thereof; a first fastener configured to apply a compressive force to prevent a rotary movement of the rotary support arm around a longitudinal axis of the support rod; a sliding plate configured to move along, and be fixed at a plurality of positions along, the longitudinal channel; a second fastener configured to apply a compressive force to prevent a displacement of the sliding plate along a length of the channel; a support bar pivotably attached to the sliding plate; and a saddle configured to support the bag of the assisted respiration device, wherein the rotary support arm is configured to be fixed by the first fastener at a plurality of positions, relative to the support rod, along the length of the longitudinal channel, and wherein the holder assembly is configured to maintain a substantially air-tight seal around the mouth of the patient, without requiring the use of a hand from a medical caregiver; and one or more straps configured for attachment, at a first end, to a first of the plurality of blocks and, at a second end, to a second of the plurality of blocks, and to secure the assisted respiration device to the patient, wherein the mask is secured to the plurality of blocks by at least one of the one or more straps.

In a fourth example embodiment, an emergency respiratory support system for providing respiratory support to a patient is disclosed, the system comprising: a base; a plurality of blocks arranged on opposite sides of a head of the patient, wherein one or more of the plurality of blocks has a vertically-oriented hole formed through a thickness thereof, the hole being configured to receive a retention tube, and the retention tube being configured to receive a first end of a support rod of the holder assembly inserted therein; an assisted respiration device comprising a bag configured to provide an air supply to the patient, an endotracheal tube (ET) bracket that is configured to be secured to an endotracheal tube inserted in a trachea of the patient, a valve connected to an external end of the endotracheal tube and configured to regulate a flow of the air supply between the bag and the endotracheal tube; a holder assembly configured for attachment to the base and to secure the assisted respiration device relative to the patient, the holder assembly comprising: a support collar attached to the support rod at a second end thereof; a rotary support arm comprising a longitudinal channel formed through a thickness thereof; a first fastener configured to apply a compressive force to prevent a rotary movement of the rotary support arm around a longitudinal axis of the support rod; a sliding plate configured to move along, and be fixed at a plurality of positions along, the longitudinal channel; a second fastener configured to apply a compressive force to prevent a displacement of the sliding plate along a length of the channel; a support bar pivotably attached to the sliding plate; and a saddle configured to support the bag of the assisted respiration device, wherein the rotary support arm is configured to be fixed by the first fastener at a plurality of positions, relative to the support rod, along the length of the longitudinal channel; and one or more straps configured for attachment, at a first end, to a first of the plurality of blocks and, at a second end, to a second of the plurality of blocks, and to secure the assisted respiration device to the patient, wherein the ET bracket is secured to the plurality of blocks by at least one of the one or more straps.

In a fifth example embodiment, an emergency respiratory support system for providing respiratory support to a patient is disclosed, the system comprising: a base; a plurality of blocks arranged on opposite sides of a head of the patient, wherein one or more of the plurality of blocks has a vertically-oriented hole formed through a thickness thereof, the hole being configured to receive a retention tube, and the retention tube being configured to receive a first end of a support rod of the holder assembly inserted therein; an assisted respiration device comprising an oxygen bag configured to provide a supply of oxygen to the patient, an oxygen mask configured to cover a mouth and/or nose of the patient, and a valve configured to regulate a flow of the supply of oxygen between the oxygen bag and the oxygen mask; and one or more straps configured for attachment, at a first end, to a first of the plurality of blocks and, at a second end, to a second of the plurality of blocks, and to secure the oxygen mask over the mouth and/or nose of the patient.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

DETAILED DESCRIPTION

Figure 1:
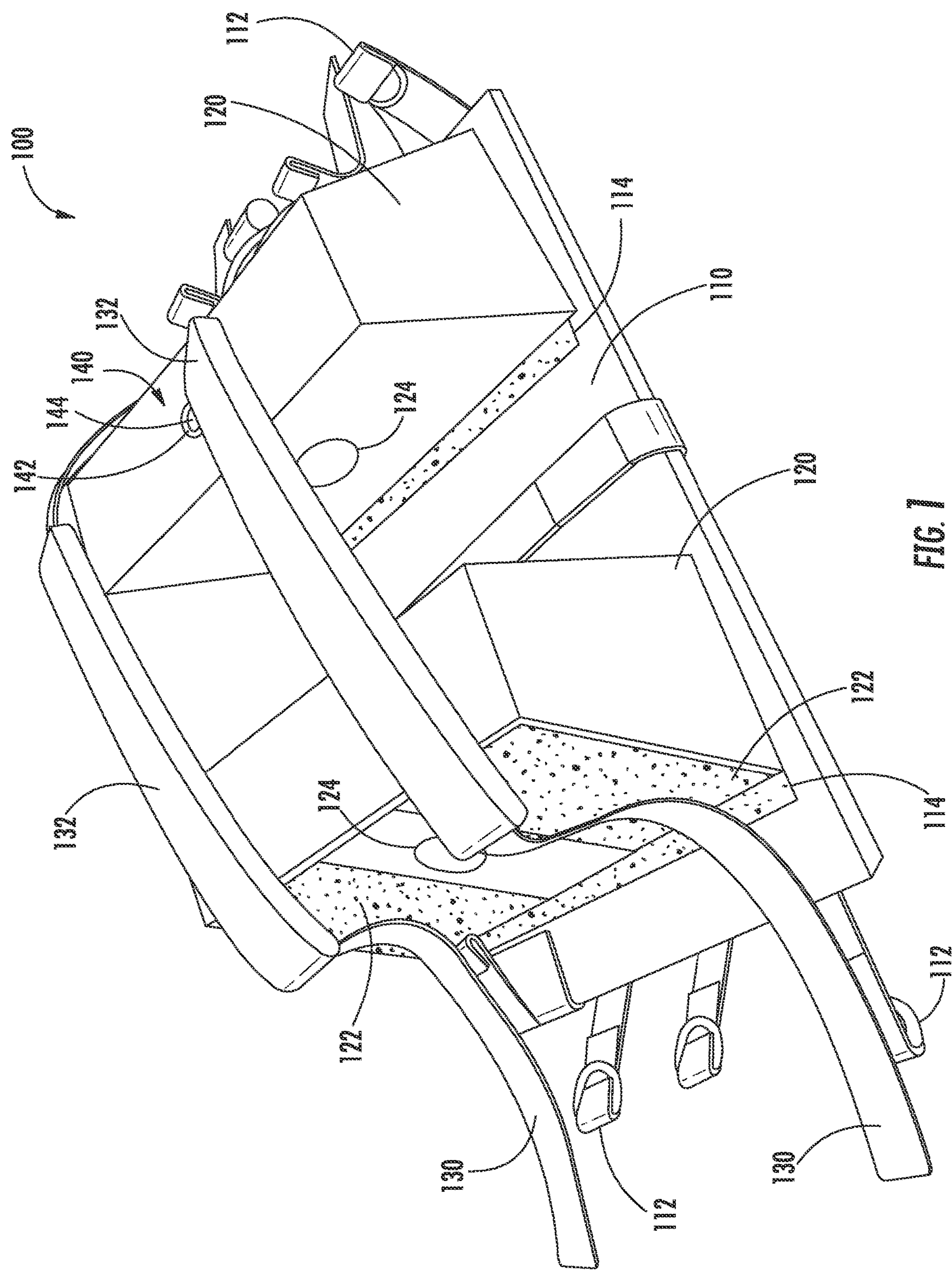
FIG. 1 is a perspective view of at least one embodiment of a head immobilizer device configured to receive an emergency respiratory support system, in accordance with the disclosure herein.

The presently disclosed subject matter now will be described more fully hereinafter, in which some, but not all, embodiments of the presently disclosed subject matter are described. Indeed, the presently disclosed subject matter can be embodied in many different forms and should not be construed as being limited to the embodiments set forth herein; rather, these example embodiments are provided so that this disclosure will satisfy applicable legal requirements.

The presently disclosed subject matter provides devices, systems and apparatuses configured to deliver emergency respiratory support therapy to patients without requiring a medical caregiver (e.g., a clinician or first responder) to hold the emergency respiratory support device in place during use. Moreover, the devices, systems, and apparatuses for providing emergency respiratory support can be applied without the difficulty associated with the application of head straps.

The disclosed devices, systems, and apparatuses for delivering emergency respiratory support to a patient can be configured in various ways to deliver the necessary ventilation (e.g., ambient air or oxygen), including, for example, as a bag valve mask (BVM), an endotracheal tube (ET), and/or an oxygen mask. In some embodiments, the systems and apparatuses for delivering emergency ventilation can comprise an automated BVM device, ventilator, or any other device or system configured to provide an air supply (e.g., with or without supplemental oxygen) to a patient. In some embodiments, the head of a patient is immobilized with, for example, a head immobilization system and the BVM is held in place by a holder assembly, with the mask seal consistently held in place by straps attached to the head immobilizer. In some embodiments, the head of a patient is immobilized with, for example, a head immobilization system and an endotracheal tube (ET) bracket is held in place by straps attached to the head immobilizer. In some embodiments, the head of a patient is immobilized with, for example, a head immobilization system and the oxygen face mask is held in place by straps attached to the head immobilizer and the mask seal is consistent.

After the devices, systems, and apparatuses for delivering emergency respiratory support to a patient have been properly applied to (e.g., secured to) a patient, a medical caregiver has the freedom to use at least one hand, but in some embodiments both hands, to perform other patient care procedures. The patient can be moved and transported without losing the seal of the oxygen delivery device mask or displacement of the endotracheal tube. As a result, medical caregivers may provide more efficient care. For example, cardiopulmonary resuscitation (CPR) may be efficiently performed by one caregiver using such an emergency respiratory support system, since one caregiver may accomplish high quality CPR without having to disengage the BVM while performing chest compressions, then reapplying the BVM each time the caregiver must ventilate the patient.

In FIG. 1, an example embodiment of a head immobilizer system, generally designated 100, is shown. The head immobilizer system 100 has a base 110, on which two regions 114 of hook and loop material are attached, and to which a plurality of base straps 112 for attaching the base 110 to a further stabilization support member (e.g., a spinal board). A head immobilizer block 120 is attached to the base at each region 114 of hook and loop material. Each head immobilizer block 120 has an ear hole 124 formed laterally through a thickness thereof. Each head immobilizer block 120 further comprises strap areas 122 of hook and loop material on the lateral outer sides thereof for securing head immobilization straps 130 thereto to immobilize the head of a patient. Each of the straps 130 in this embodiment has head strap pads 132 affixed (e.g., movably) thereto for patient comfort. At least one of the head immobilizer blocks 120 have a hole, generally designated 140, formed therein through at least a portion of a vertical thickness thereof. A retention tube 142 is disposed vertically within the hole 140. The upper surface of retention tube 142 can be flush with, recessed within, or extend beyond the upper surface of the head immobilizer block 120 through which hole 140 is visible. The retention tube 142 has an axially oriented hole formed along the length thereof to receive and secure a holder for a respiratory support device (e.g., a bag of a BVM) to the head immobilizer system 100. While both of the head immobilizer blocks 120 may have hole 140 formed therein, the symmetrical nature of the attachment of the head immobilizer blocks 120 to the base 110 allows for the head immobilizer blocks 120 to be rearranged to allow for hole 140 to be present on either side of the patient's head. The respective hook or loop portions of hook and loop material can be applied to any of the areas described hereinabove as comprising the hook and loop material.

Figure 2:
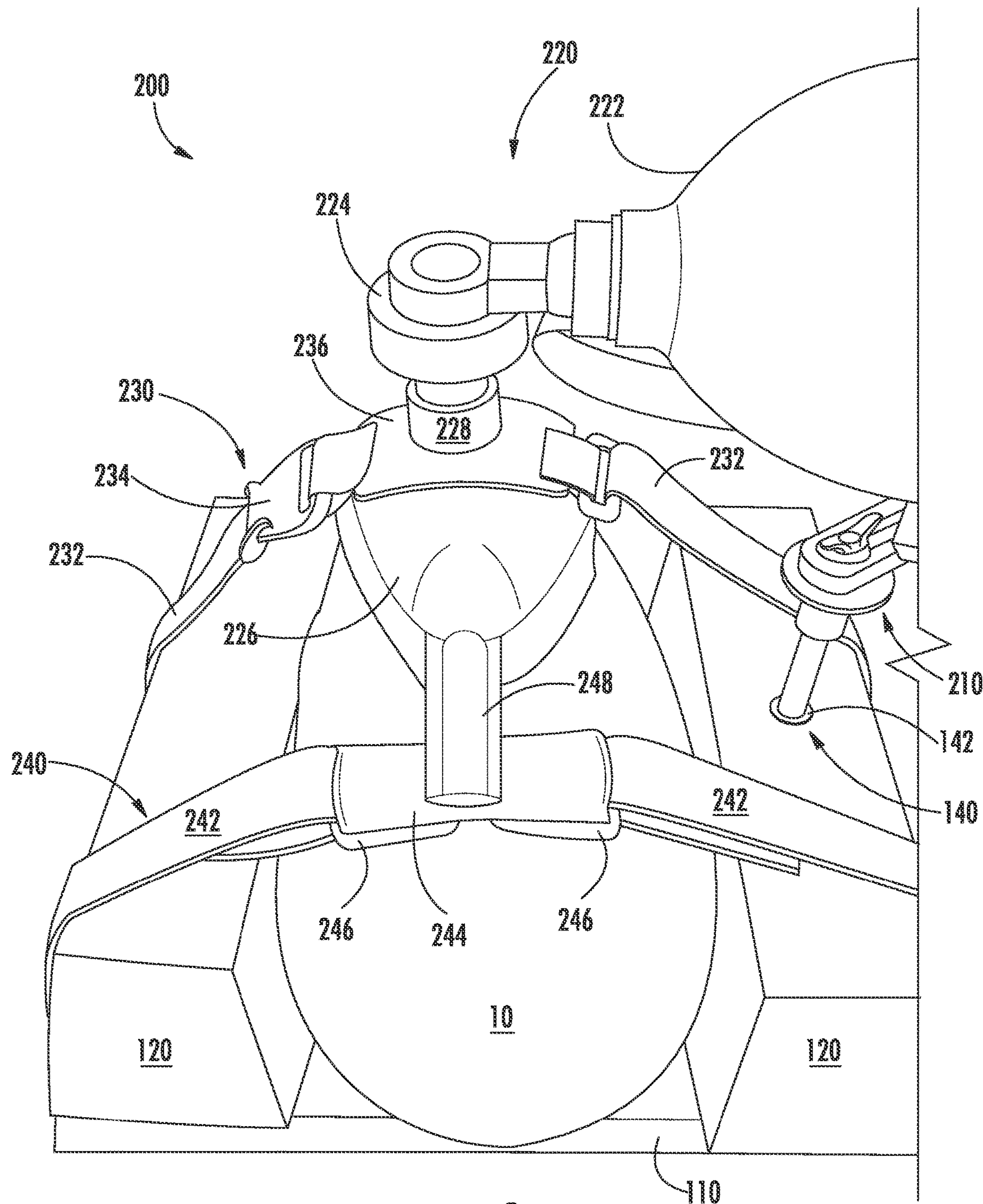
FIG. 2 is a perspective view of a first example embodiment of an emergency respiratory support system secured to a head immobilizer for providing emergency respiratory support to a patient, in accordance with the disclosure herein.
Figure 4:
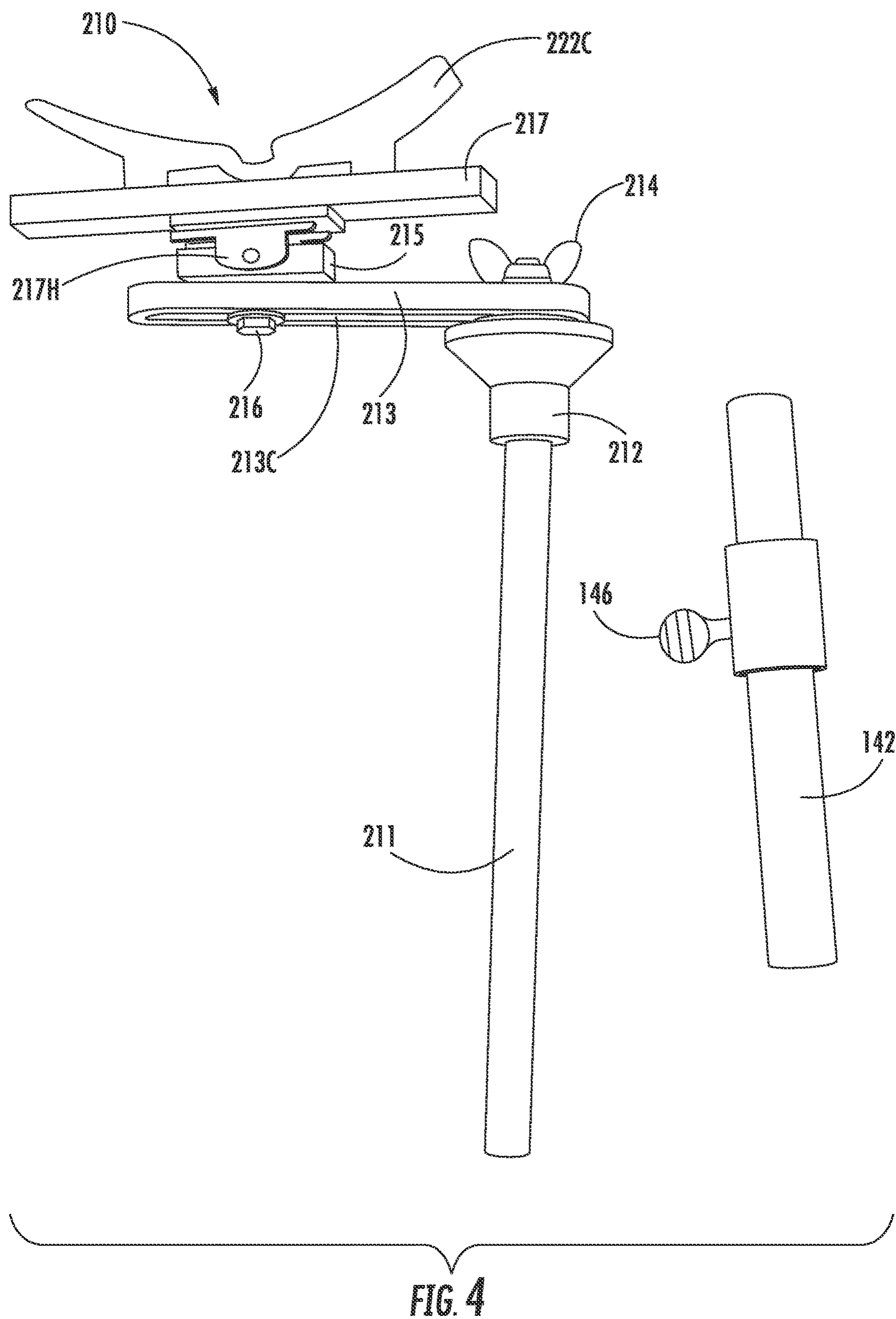
FIG. 4 is a side perspective view of an example embodiment of a part of the emergency respiratory support system of FIGS. 2 and 3 for securing a bag in a fixed position relative to the patient's head, in accordance with the disclosure herein.

A first example embodiment of an emergency respiratory support system, generally designated 200, is shown in FIG. 2, including base 110 and head immobilizer blocks 120 as described and shown relative to FIG. 1. In this embodiment, at least one head immobilizer block 120 has a hole, generally designated 140, formed therein, in which a retention tube 142 (or sleeve) is installed. Retention tube 142 is configured to receive holder assembly, generally designated 210, to secure holder assembly 210 relative to head immobilizer block 120. In some embodiments, such as is shown in FIG. 4, the holder assembly 210 is stabilized by a set screw (e.g., 146) or other securing mechanism.

The holder assembly 210 is generally configured to attach to one of the head immobilization blocks 120 and provide a support and securing mechanism for positioning and holding an assisted respiration device, generally designated 220, which in this embodiment is configured as a bag valve mask (BVM) device, in position relative to a head of a patient 10 that is secured between the head immobilizer blocks 120. When in use, the holder assembly allows the assisted respiration device 220 to be securely held in place without requiring a medical caregiver to hold the assisted respiration device 220 in proper alignment over the patient's nose and mouth. Instead, when held in place by the holder assembly 210, a medical caregiver only needs to manipulate the bag 222 to provide emergency respiratory ventilation to the patient 10. When actuated (e.g., squeezed), the bag 222 provides a supply of air, which can include supplemental oxygen provided by an oxygen source, or air with an oxygen content substantially identical to the oxygen content of ambient air to the patient 10 through a valve 224 attached to a mask 226 through mask coupler 228.

In the embodiment shown in FIG. 2, a mask strap assembly, generally designated 230, is used to secure the mask 226 of the assisted respiration device 220 over the nose and mouth of the patient 10 to create an air-tight, or substantially air-tight, seal therearound. The mask strap assembly 230 comprises a pliable mask attachment 236 that surrounds and is, in some embodiments, placed over and around mask coupler 228; this mask attachment can be a durable piece of fabric that is attached at both lateral sides thereof, by one or more quick releases 234, to straps 232 that are configured to engage, via a hook and loop fastening material affixed on one or more (e.g., both) sides thereof, with a corresponding hook and loop material (e.g., 122, FIG. 1) on the sides of head immobilizer blocks 120. In this manner, the straps 232 can easily and quickly be attached to and/or detached from the head immobilizer, and the amount of pressure applied to the mask 226 to create a suitable seal around the nose and mouth of the patient 10 can be varied by adjusting the amount of force used in securing the straps 232 to the head immobilizer blocks 120.

In the embodiment of FIG. 2, the mask 226 of the assisted respiration device 220 also comprises a forehead strap assembly 240 for securing the upper portion of the mask 226 over the region around the nose of the patient 10. The mask 226 is connected to a forehead bracket 244 by a mask bridge 248. The forehead bracket 244 has one or more (e.g., two) forehead pads 246 to provide enhanced patient comfort while secured to the patient. The forehead bracket 244 has, at each lateral side thereof, a forehead strap 242 attached thereto to secure the forehead strap assembly 240 to the head immobilizer blocks 120. Just as was described regarding the mask strap assembly 230, the forehead straps 242 have hook and loop fastening material affixed on one or more (e.g., both) sides thereof, which is securable to corresponding hook and loop material (e.g., 122, FIG. 1) of the head immobilizer blocks 120. A quick release can be provided for the forehead strap assembly to couple the one or more forehead straps to the forehead bracket 244.

Figure 3:
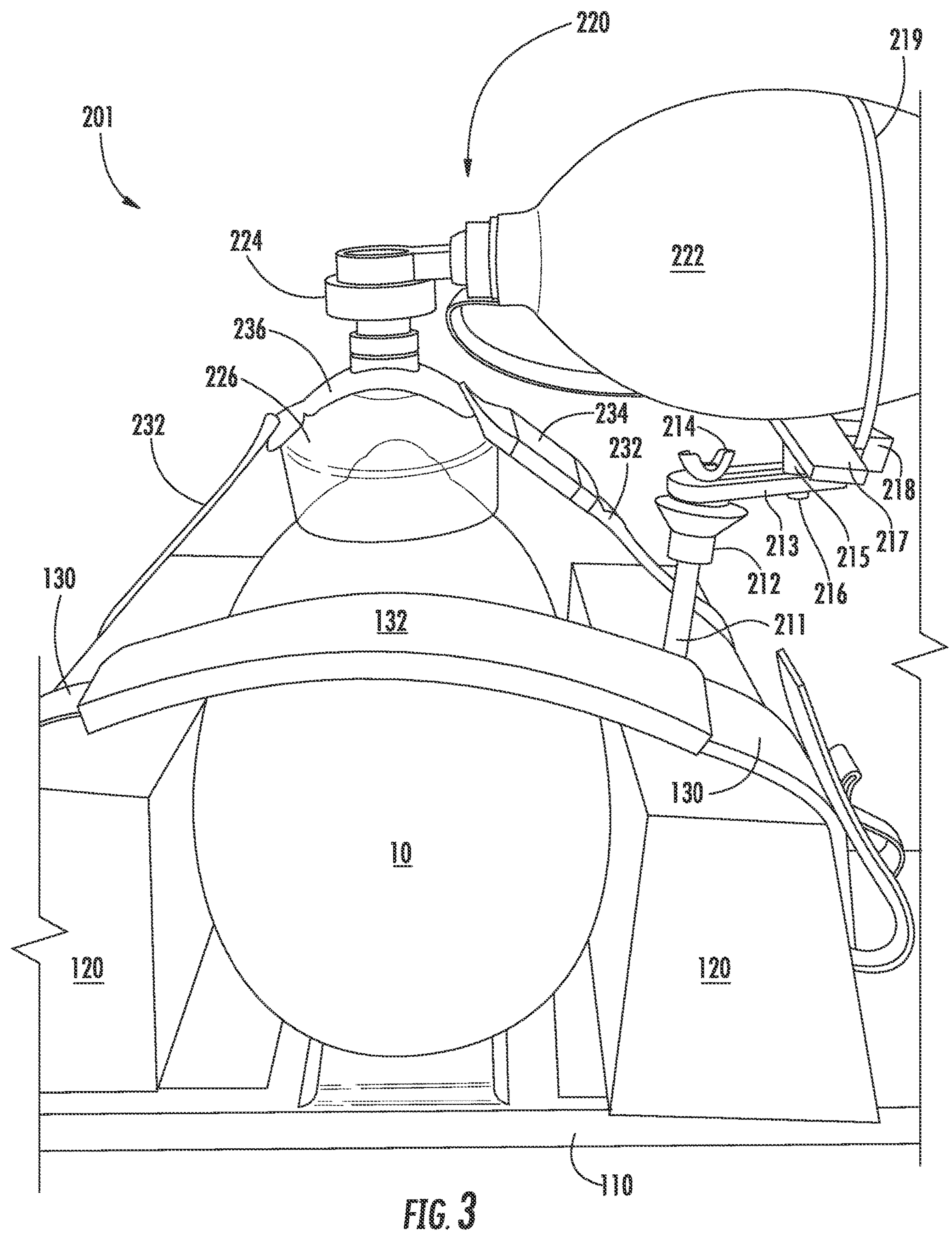
FIG. 3 is a perspective view of a second example embodiment of an emergency respiratory support system secured to a head immobilizer for providing emergency respiratory support to a patient, in accordance with the disclosure herein.

In the second example embodiment of FIG. 3, the assisted respiration device 220 is provided in much the same way as was described regarding the illustration of the first example embodiment of FIG. 2, however forehead strap assembly 240 is replaced with a conventional head immobilization strap 130 with a head strap pad 132 attached thereto. The head immobilization strap 130 is attached, via a hook or loop fabric material, to a corresponding hook or loop material on the lateral outboard sides of head immobilizer blocks 120, as shown in FIG. 1. Furthermore, in the embodiment of FIG. 3, the quick release 234 is arranged on an opposite side of the mask 226 from that shown for FIG. 2. Additionally, as will be described hereinbelow, the holder assembly 210 is shown and described in greater detail with respect to FIG. 3, but it is noted that the holder assembly of FIGS. 2 and 3 are substantially identical to each other, with various deviations being permissible as understood by those having ordinary skill in the art.

A support rod 211 is inserted within the hole 144 (see, e.g., FIG. 1) provided by retention tube 142 (see, e.g., FIG. 1) and held vertically in place by, for example, a set screw (e.g., 146, see FIG. 4). A rotary support arm 213 is attached, via a support collar 212 on the distal (e.g., upper) end of support rod 211. Support collar 212 may be integrally formed in a single piece with (e.g., in a monolithic manner) support rod 211 or, in some embodiments, may be threadably engaged onto support rod 211. Support collar 212 has a threaded member (not shown) that extends substantially coaxial to the support rod 211 such that a support arm fastener 214 can threadably engage with the threaded member to apply a clamping force to rotary support arm 213 to secure the rotary support arm 213 in a fixed position relative to the patient 10 and the support rod 211. The rotary support arm 213 has at least one channel (e.g., a slot, see 213C in FIG. 4) formed along the length thereof, such that the rotary support arm 213 can move to allow the support arm fastener 214 to be fastened at substantially any longitudinal position along the length thereof. A sliding plate 215 is attached, via a sliding plate fastener 216 engaging with a threaded member associated with the sliding plate 215, to an upper side of the rotary support arm 213. Sliding plate 215 has a retention hook 218 formed thereon, which is configured to engage with elastic retainer 219, which can be integrally formed with bag 222 in some embodiments and is configured to retain bag 222 in a position on top of a bag saddle (see, e.g., 222C, FIG. 4) or cushion to be in a position for actuation by a medical caregiver. In some embodiments, elastic retainer can be a rubber band. A support bar 217 is connected on an upper surface of sliding plate 215 to support the bag 222.

Referring to FIG. 4, the holder assembly 210 is shown in greater detail. The retention tube 142 has an axially oriented hole formed along the length thereof to receive and secure a holder for a respiratory support device (e.g., a bag of a BVM) to the head immobilizer system 100 (see, e.g., FIG. 1). Retention tube 142 is configured to receive holder assembly, generally designated 210, within an axial hole formed in retention tube 142 to secure holder assembly 210 therein using set screw 146. Support rod 211 is inserted within the hole 144 (see, e.g., FIG. 1) provided by retention tube 142 (see, e.g., FIG. 1) and held vertically in place by, for example, a set screw (e.g., 146, see FIG. 4). A rotary support arm 213 is attached, via a support collar 212 on the distal (e.g., upper) end of support rod 211. Support collar 212 may be integrally formed in a single piece with (e.g., in a monolithic manner) the support rod 211 or, in some embodiments, may be threadably engaged onto the support rod 211. Support collar 212 has a threaded member (not shown) that extends substantially coaxial to the support rod 211 such that a support arm fastener 214 can threadably engage with the threaded member to apply a clamping force to rotary support arm 213 to secure the rotary support arm 213 in a fixed position relative to the patient and the support rod 211. The rotary support arm 213 has at least one longitudinal channel 213C (e.g., a slot) formed along the length thereof, such that the rotary support arm 213 can move to allow the support arm fastener 214 (e.g., a wing nut) to be fastened at substantially any longitudinal position along the length thereof. A sliding plate 215 is attached, via a sliding plate fastener 216 engaging with a threaded member associated with the sliding plate 215, to an upper side of the rotary support arm 213. In some embodiments, sliding plate fastener 216 may be a thumb screw that passes through the channel 213C formed along the length of rotary support arm 213, so that the threaded portion thereof passes into and is threadably engaged with a threaded recess integrally formed in sliding plate 215. Sliding plate 215 is displaceable along the length of the channel 213C formed in rotary support arm 213. Sliding plate 215 is connected to a support bar 217 at a pivot point 217H (e.g., a pin hinge joint) and is configured to retain bag 222 in a position on top of a bag saddle 222C or cushion to be in a position for actuation by a medical caregiver. The support rod 211, particularly when inserted into and engaged to a head immobilizer block (e.g., 120, FIGS. 2 and 3), provides a stable platform upon which to mount the assisted respiration device 220.

Figure 5:
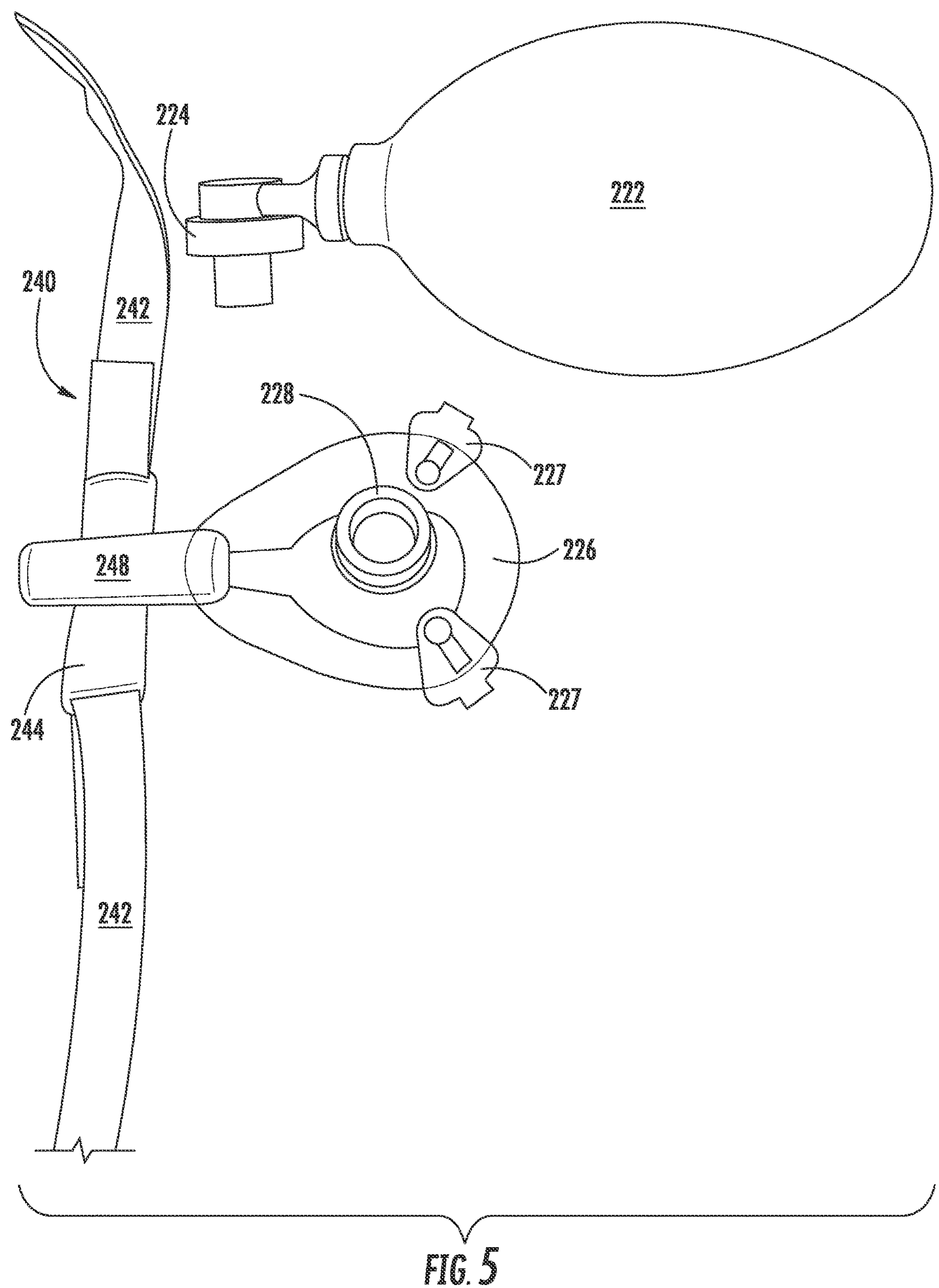
FIG. 5 shows a portion of the emergency respiratory support system of FIG. 2, in accordance with the disclosure herein.

FIG. 5 illustrates the components of the assisted respiration device shown in FIG. 2. The mask 226 is connected to the forehead strap assembly, generally designated 240, by mask bridge 248. The mask 226 has one or more auxiliary attachment points 227 to which an auxiliary strap (see, e.g., 470, FIGS. 8 and 9) can be attached to secure the mask 226 over the mouth and nose of the patient. The components of forehead strap assembly 240 are substantially identical to the illustrations shown in FIG. 2. The mask 226 has a mask coupler 228 for connecting the mask 226 to the valve 224 so that a supply of ambient air can be provided to a patient from bag 222 to provide respiratory support to the patient in a medical emergency. The mask coupler 228 can comprise a female joining member configured to receive a male joining coupler member on the valve 224 such that they (e.g., the mask coupler 228 and the corresponding part of the valve 224) can be slidingly engaged, or otherwise securely coupled, with each other to create a pathway or conduit for airflow from the bag into the mask, via the valve 224.

Figure 6:
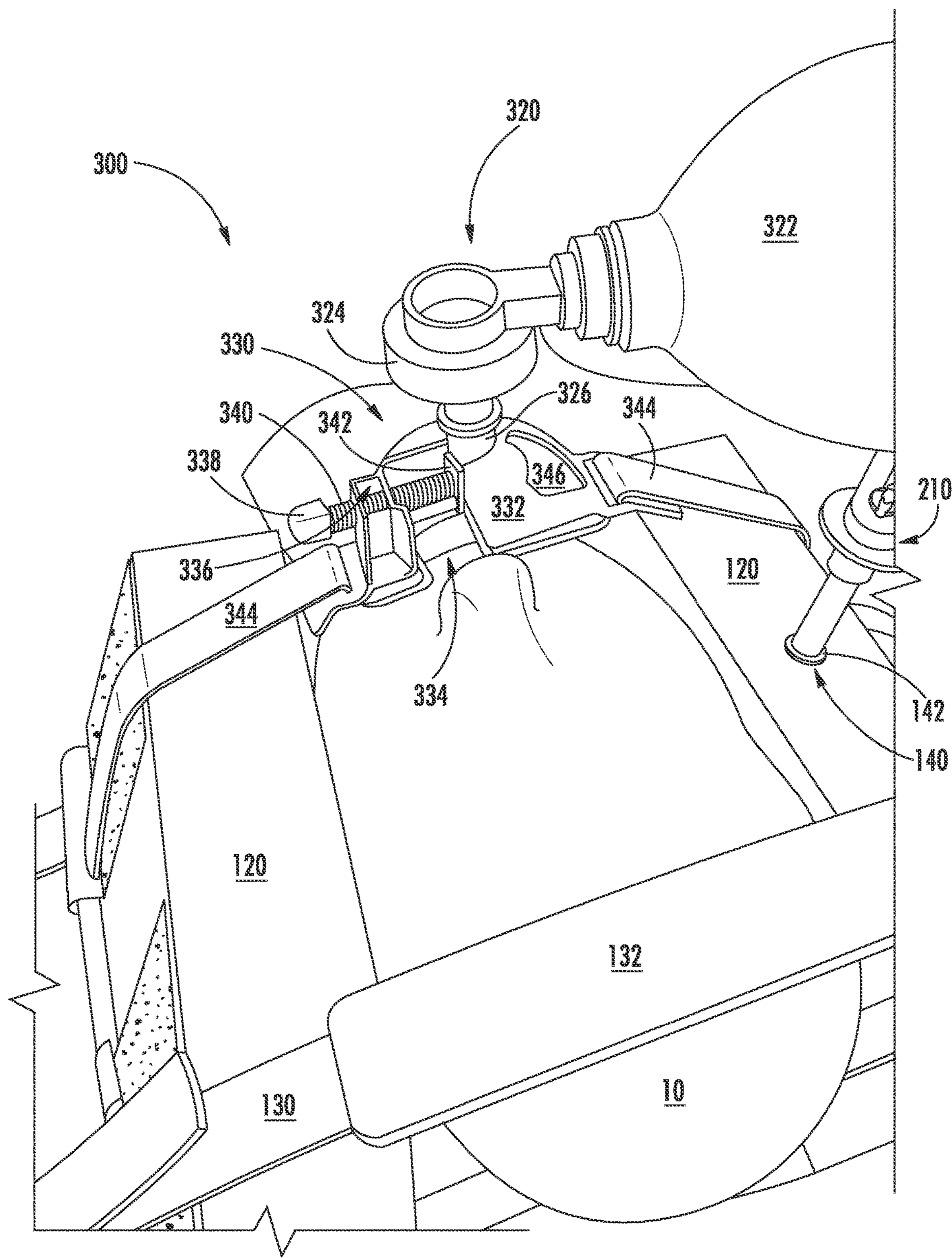
FIG. 6 is a perspective view of a third example embodiment of an emergency respiratory support system secured to a head immobilizer for providing emergency respiratory support to a patient, in accordance with the disclosure herein.
Figure 7:
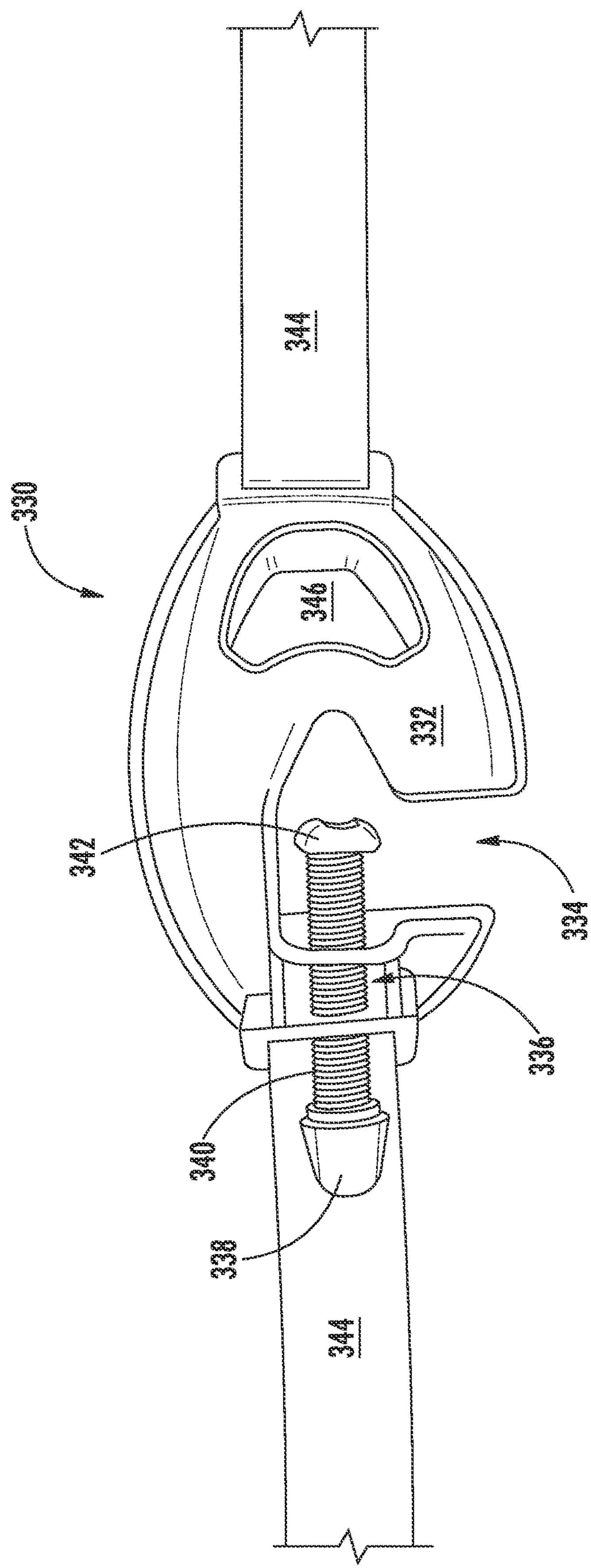
FIG. 7 is a top view of an example embodiment of an endotracheal tube (ET) bracket, as shown secured to a patient in FIG. 6, in accordance with the disclosure herein.

Another example embodiment of an emergency respiratory support system, generally designated 300, is illustrated in FIGS. 6 and 7. System 300 comprises an endotracheal tube (ET) bracket assembly, generally designated 330, that is provided in place of the mask in the previously described example embodiments. The ET bracket assembly 330, as disclosed herein comprises an ET bracket 332 configured to hold an endotracheal tube 326 that is inserted into a trachea of a patient 10 in a stationary position relative to the trachea of the patient. A first end of the endotracheal tube 326 is located within the trachea of the patient 10 and a second end thereof is coupled to a valve 324. The ET bracket 332 can be provided with one or more straps 344 extending laterally away therefrom, which are configured to be secured, in a substantially similar manner to that of the previously described embodiments of FIGS. 2 and 3, to a head immobilizer block 120 using hook and loop fastening material, or any other suitable fastening mechanism. A holder assembly 210, substantially similar to holder assemblies described in FIGS. 2 through 4, is provided to hold, position, and secure a bag 222 in a position so as to be coupled to the valve 224 and endotracheal tube 226.

The ET bracket assembly 330 is advantageous in that it can be applied to a patient 10 whose head is already immobilized without having to move the patient's head to fully wrap a head strap system around the patient's head. This advantage is achieved, at least in part, by the formation of an ET insertion cavity 334 in, and coincident with at least one edge of, the ET bracket 332. This allows for the ET bracket 332 to be placed around the endotracheal tube 226 without having to be placed over top of the endotracheal tube 226 (e.g., with the endotracheal tube 226 passing through a discrete hole of the ET bracket 332), thereby preventing any undesired axial displacements of the endotracheal tube 226 within the trachea of the patient 10. The endotracheal tube 226 is secured relative to the ET bracket 332 by applying a compressive force, using a threaded rod with a thumb screw 338 with an ET screw plate 342 at an end thereof, to the endotracheal tube 226. The ET screw threaded portion 340 passes through the ET screw support cavity 336, which has a generally rectilinear cross-section, and has a rotatably pivotable ET screw plate 342 (e.g., so as to be able to remain in a rotatably static position when engaged against the endotracheal tube 326 as thumb screw 338 and/or threaded portion 340 are rotated) attached at a second end of the ET screw threaded portion 340. An ET screw head 338 is affixed to a first end of ET screw threaded portion 340. The longitudinal position of ET screw plate 342 and, accordingly, the compressive force applied to fix the endotracheal tube 326 to ET bracket 332 varies based on the direction and amount that ET screw head 338 is turned. A viewport 346 is provided in ET bracket 332 to allow a caregiver to view the mouth of the patient 10 during operation. The straps 344 can, in some aspects, be made from a material (e.g., a "loop" material) which adheres easily to the hook surface at the attachment regions (see, e.g., 114, FIG. 1) on the head immobilizer blocks 120. The head immobilization strap(s) 130 and head strap pad 132 are substantially identical to those which were described, respectively, in FIGS. 1 and 3, and will not be described further herein, beyond stating that the head immobilizer strap(s) are attached, via a hoop and look fastening material or any suitable alternative, to one of the head immobilizer blocks 120 on each side of the head of the patient 10.

Figure 8:
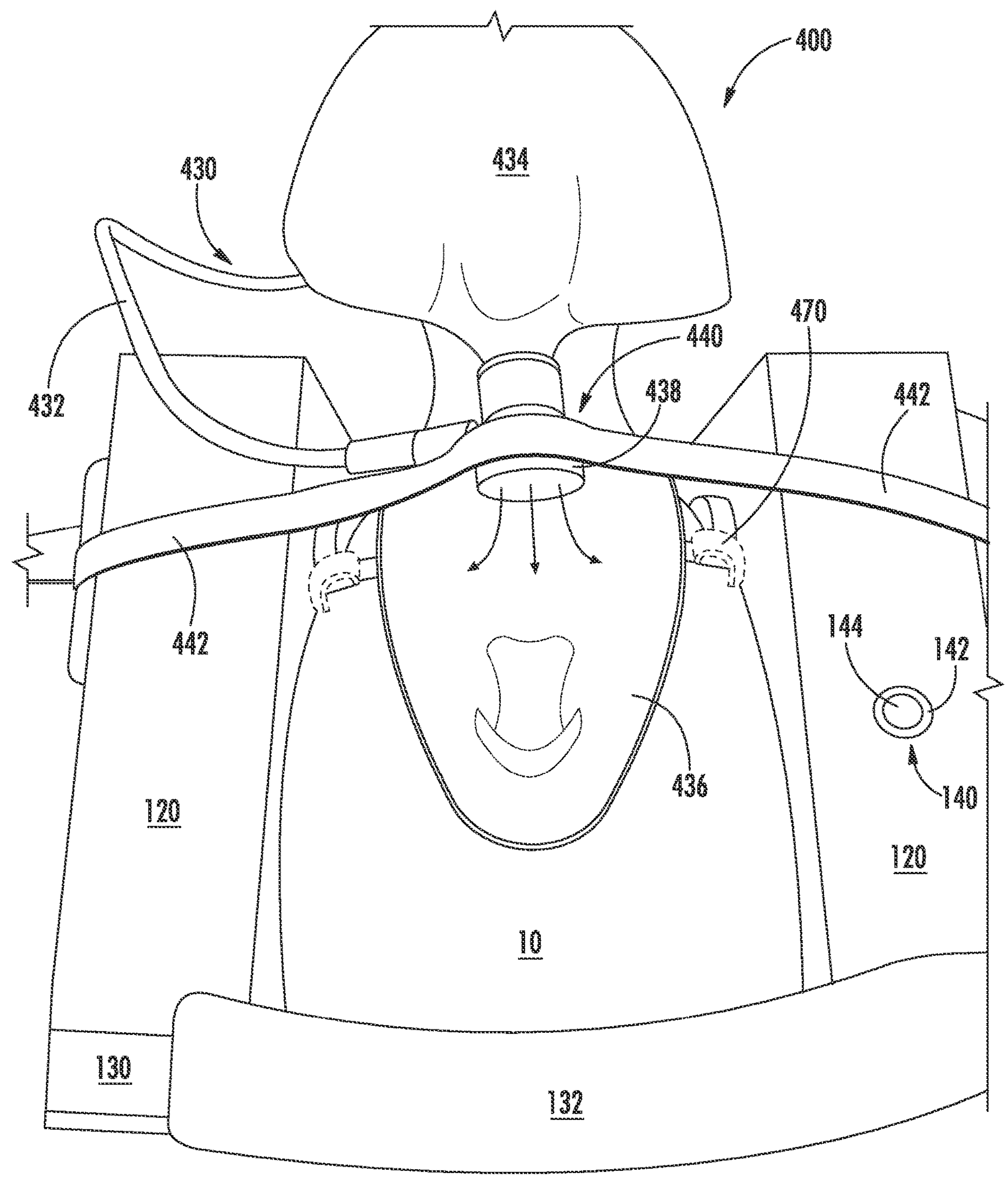
FIG. 8 is a perspective view of a fourth example embodiment of an emergency respiratory support system secured to a head immobilizer for providing emergency respiratory support to a patient, in accordance with the disclosure herein.
Figure 9:
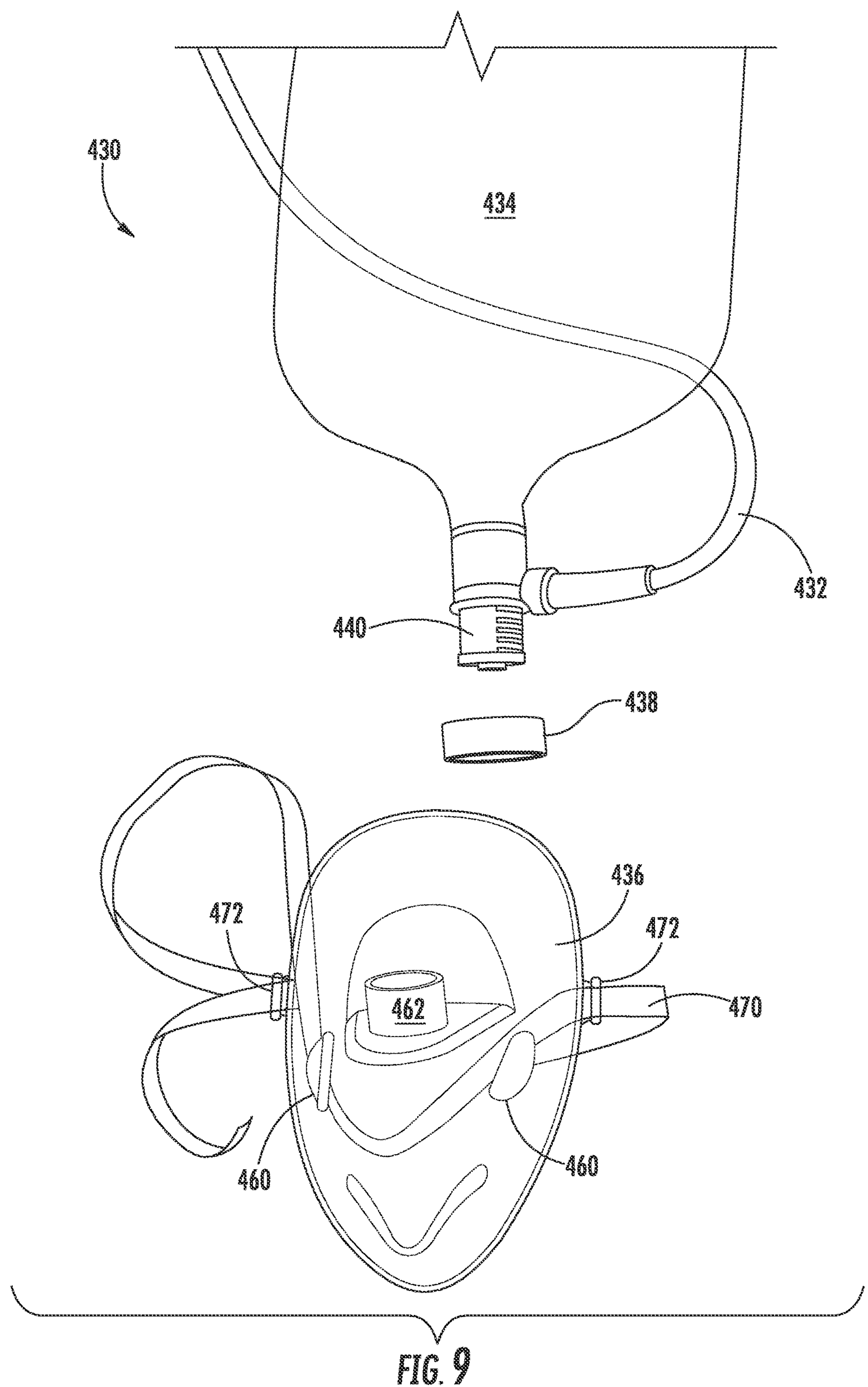
FIG. 9 is a top perspective view of an example embodiment of a mask, valve, and bag for providing emergency oxygen to a patient, as shown secured to a patient in FIG. 8, in accordance with the disclosure herein.

In still another example embodiment of an emergency respiratory support system, generally designated 400 as shown in FIGS. 8 and 9, an assisted respiration device, generally designated 430, is shown to provide a supply of oxygen to a patient 10. The assisted respiration device 430 comprises an oxygen mask 436, a valve 440, and oxygen bag 434, with a ring-shaped coupler 438, which is fully or partially covered by a hook or loop surface and is positioned on, or engaged to, mask inlet a port on valve 440 to insert the oxygen supply line 432. In this embodiment, a single mask attachment strap 442 with hook or loop surface is attached to the corresponding hook or loop surface of the coupler 438, with opposing ends of the strap 442 then securely fastening to the head immobilizer blocks 120 with hook/loop surfaces on the sides thereof. The strap 442 can be made from a material which adheres easily to the hook surface (or, conversely, the loop surface) of the head immobilizer blocks 120. The mask 436 is, in some embodiments, an inflated mask or a mask from a softer, more efficient sealing material, such as silicone, similar to those currently used in emergency CPAP systems. The head immobilization strap(s) 130 and head strap pad 132 are substantially identical to those which were described, respectively, in FIGS. 1 and 3, and will not be described further herein, beyond stating that the head immobilizer strap(s) are attached, via a hoop and look fastening material or any suitable alternative, to one of the head immobilizer blocks 120 on each side of the head of the patient 10.

In some embodiments, the mask 436 can have two straps added, which are designed to be secured to the hook surface of the head immobilizer. The straps can be made from a material which adheres easily to the hook surface of the head immobilizer. The mask can be used with or without forehead cushion and straps, often referred to as a "full face mask," as is shown in the embodiment of FIG. 2 discussed hereinabove. In some other embodiments, where it is desired to augment the single strap 442, it is contemplated that the mask may have a mask auxiliary strap 470 that is connected to the sides of the mask 436 at two auxiliary strap attachment points 472 and is configured to be secured around the rear of the head of the patient 10.

Figure 10:
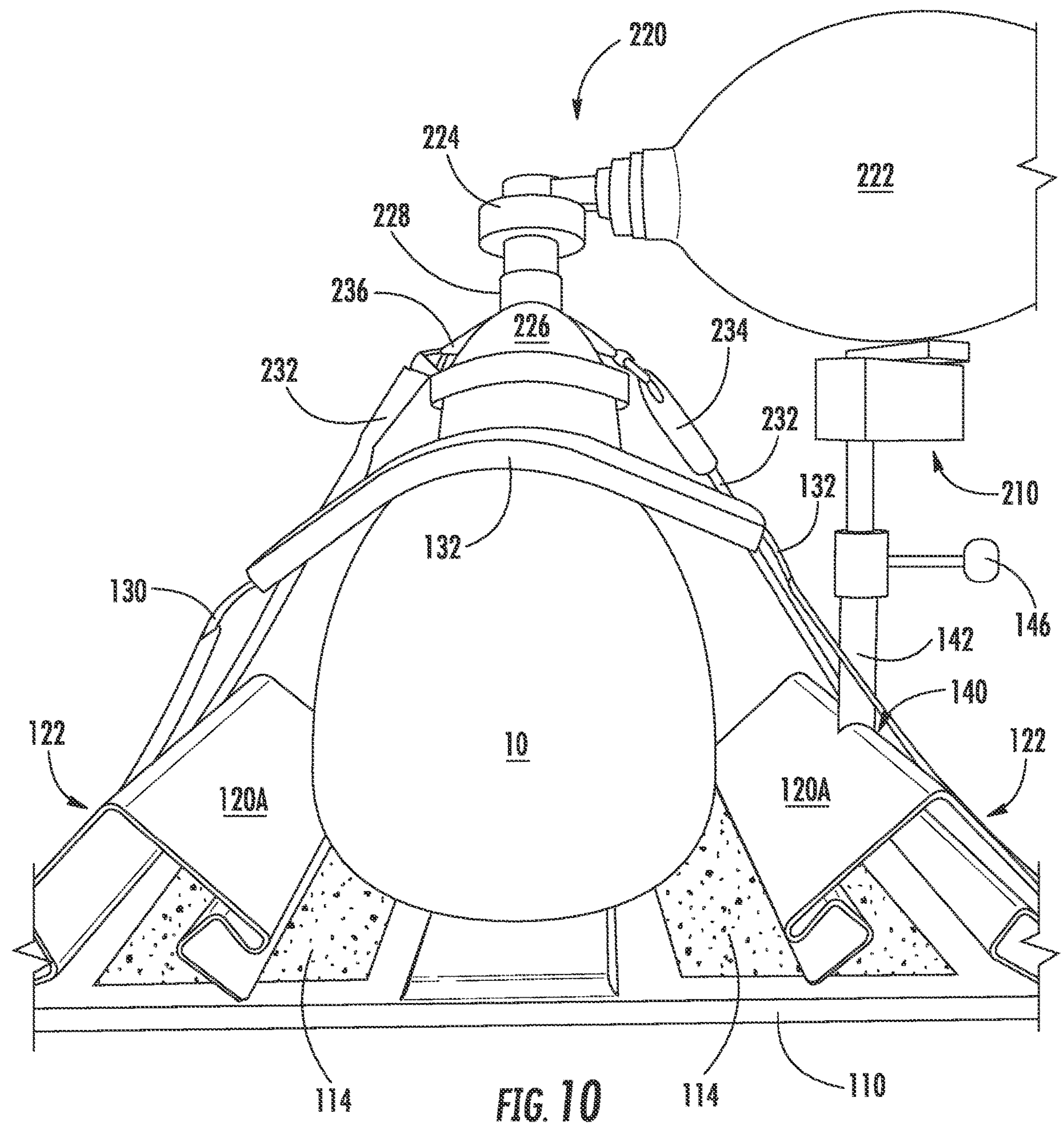
FIG. 10 is a perspective view the example embodiment of the emergency respiratory support system of FIG. 3, without being secured to a head immobilizer, in accordance with the disclosure herein.
Figure 11:
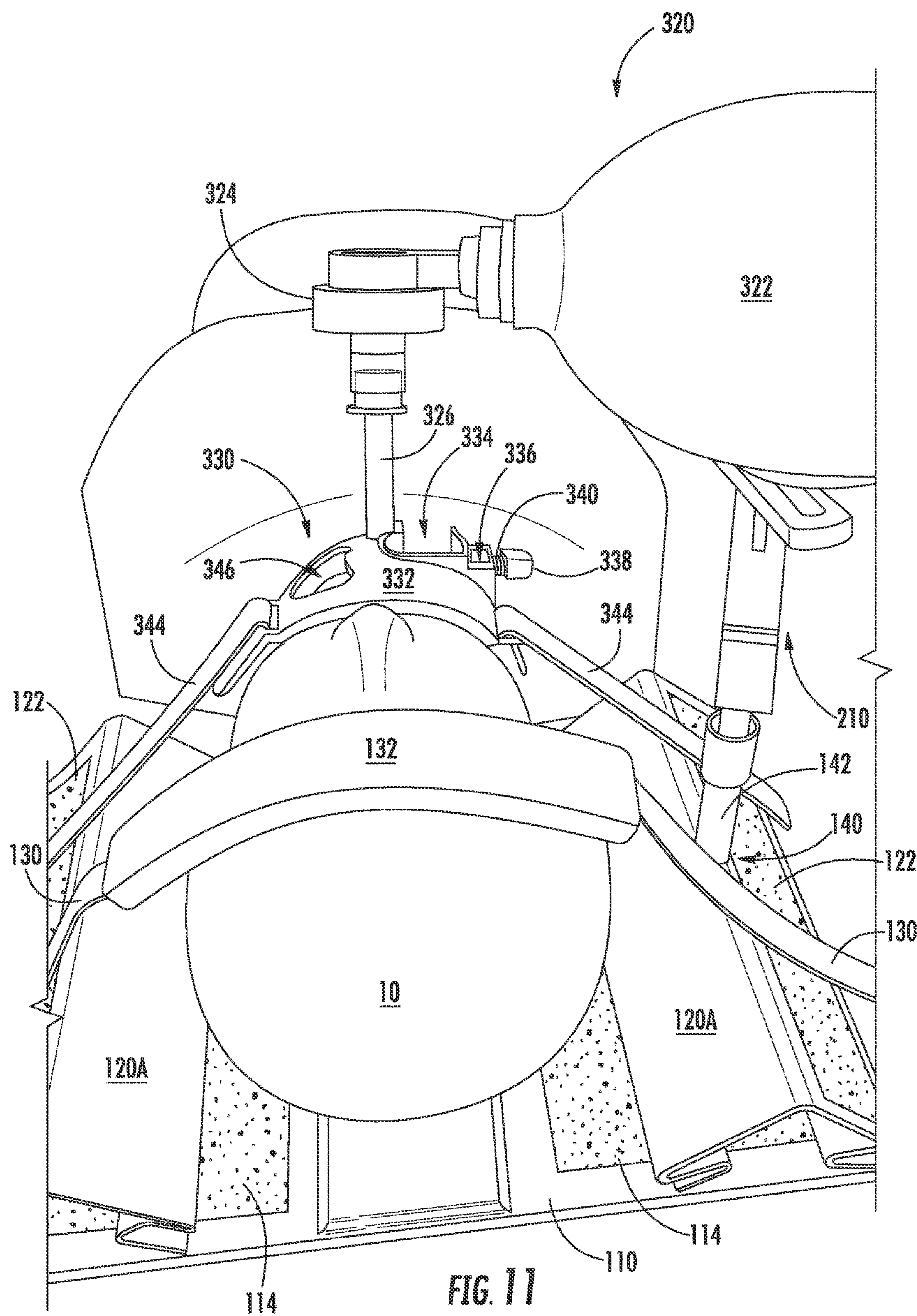
FIG. 11 is a perspective view the example embodiment of the emergency respiratory support system of FIG. 6, without being secured to a head immobilizer, in accordance with the disclosure herein.

Referring now to FIGS. 10 and 11, further example embodiments that are operable in a substantially identical manner to those discussed hereinabove are shown, however the example embodiments of FIGS. 10 and 11 are configured for use in instances where respiratory support is needed, but complete head immobilization is not needed. As such, instead of using head immobilizer blocks, one strap attachment block 120A is provided on either side of the head of the patient 10, and are each attached (e.g., removably) to base 110. The strap attachment blocks 120A are shown with generally triangular cross-sectional shapes, but any suitable cross-sectional shape may be used instead. As denoted by the use of commonly numbered elements as were described in FIG. 2, the assisted respiration device, generally designated 220, and its constituent components shown in the embodiment in FIG. 10 operate in a substantially similar manner as was described relative to the description of the embodiment of FIG. 2. The straps 130 and 232 used to secure the forehead and mask/chin of the patient, respectively, have a hook or loop material on at least one surface thereof that is configured to engage with and be secured to the strap areas 122 on strap attachment blocks 120A, each of which have a hook or lop material attached thereto. The strap attachment blocks 120A are secured (e.g., removably) to base 110. In some embodiments, strap attachment blocks 120A may be secured via a hook and loop interface with regions 114 of hook and loop material on base 110, but any suitable type of attachment capable of providing substantially rigid attachment of the strap attachment blocks 120A to base 110 may be used. As shown, at least one of the strap attachment blocks 120A has a hole formed therein, through which retention tube 142 passes to be secured thereto. Furthermore, holder assembly 210 is rigidly held in place within retention tube 142 using the set screw 146.

Figure 12:
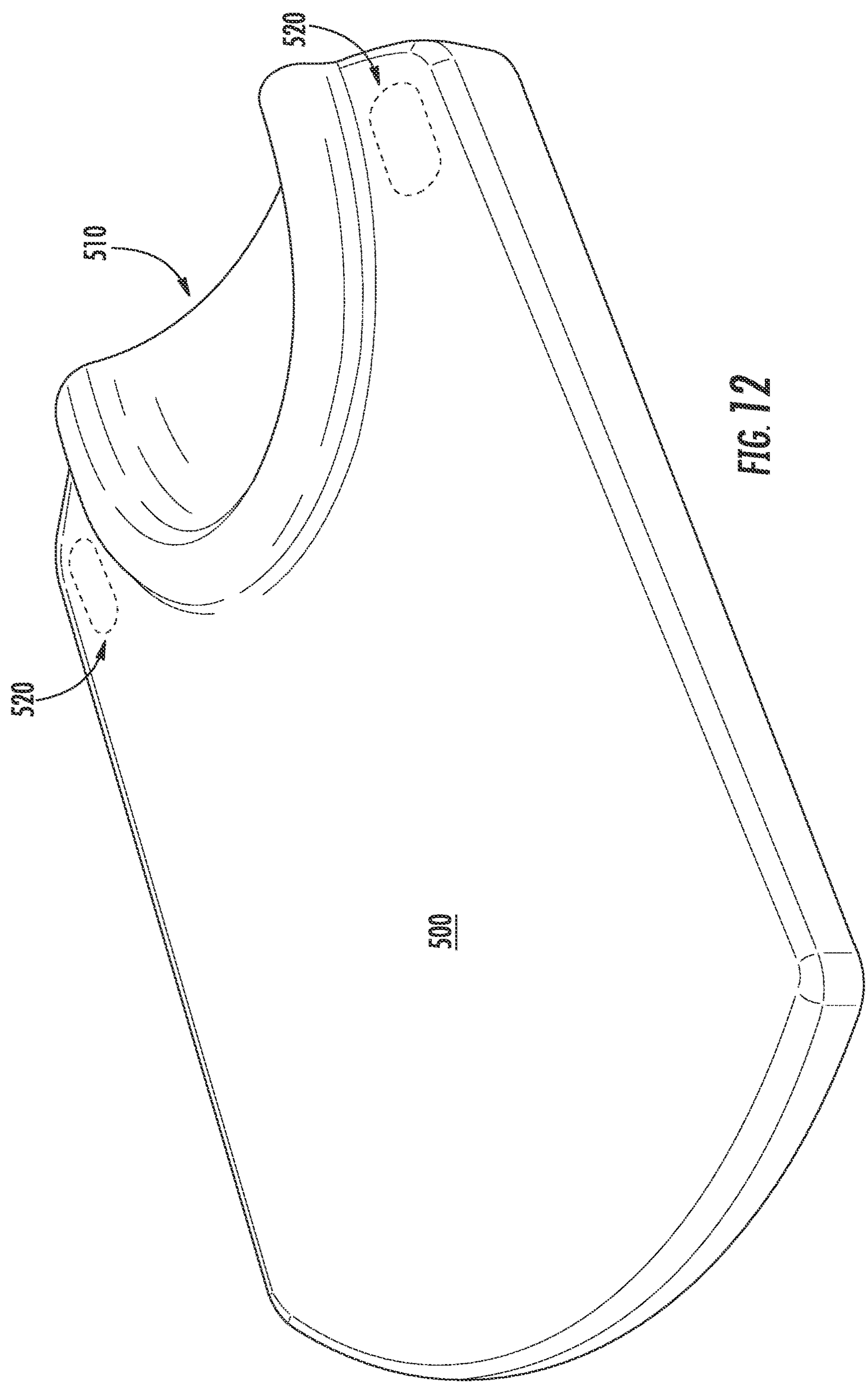
FIG. 12 is an example embodiment of a cardiopulmonary resuscitation (CPR) board, to which any of the example embodiments of the emergency respiratory support systems in any of the figures above may be attached to provide emergency respiratory support to a patient on the CPR board, in accordance with the disclosure herein.

In FIG. 12, an example alternative structure is shown, to which any of the emergency respiratory support systems disclosed hereinabove may be secured for providing respiratory support to a patient by a medical caregiver. In the embodiment shown, a cardiopulmonary resuscitation (CPR) board 500 is shown. Example attachment points, generally designated 520, are shown in broken line. Other attachment points are contemplated. In some embodiments, through-holes may be provided for a holder assembly to be attached to CPR board 500 (or any similar suitably rigid device) using a threaded screw, or similar fastener. In some embodiments, a clamp member (e.g., similar to a binder clip) may be provided on an end of the holder assembly so that the clamp member can be removably held in place on the CPR board 500 frictionally by an interference fit (e.g., the thickness of the CPR board is greater than the distance between the arms of the clamp member at the point of attachment of the holder assembly). As long as the point at which the holder assembly is sufficiently close to the head of the patient (e.g., near patient head region, generally designated 510) to allow for the mask, ET bracket, etc. to be properly secured to the face of the patient to provide the needed respiratory support, any location for attachment of the holder assembly to a supporting structure (e.g., CPR board 500) may be selected, as will be understood by those having ordinary skill in the art.

None of the disclosed designs and configurations of the head immobilizer, BVM, ET tube bracket or oxygen face mask affect the functionality or intended use of the devices. However, the designs and configurations of each allows for a medical caregiver (e.g., a clinician and/or a first responder) to use the devices in a hands-free manner allowing additional medical care to be provided without restriction.

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a component" includes a plurality of such components, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the terms "about" and/or "substantially," when referring to a value or to an amount of a composition, mass, weight, temperature, time, volume, concentration, percentage, length, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

It will be understood that various details of the presently disclosed subject matter may be changed without departing from the scope of the presently disclosed subject matter. Furthermore, the foregoing description is for the purpose of illustration only, and not for the purpose of limitation.

PARTS LIST

10—Patient
100—Head Immobilizer System
110—Base
112—Base Strap(s)

114—Region(s) of Hook and Loop
120—Head Immobilizer Block(s)
120A—Strap Attachment Block(s)
122—Strap Area(s) of Hook and Loop
124—Ear Hole
130—Head Immobilization Strap(s)
132—Head Strap Pad(s)
140—Hole (for Retention Tube 142)
142—Retention Tube
144—Hole (for Holder 210)
146—Set Screw
200—Emergency Respiratory Support System (1st Embodiment)
201—Emergency Respiratory Support System (2nd Embodiment)
210—Holder Assembly
211—Support Rod
212—Support Collar
213—Rotary Support Arm
214—Rotary Support Arm Fastener
215—Sliding Plate
216—Sliding Plate Fastener
217—Support Bar
217A—Support Bar Pivot
218—Retention Hook
219—Elastic Retainer
220—BVM (Assisted Respiration Device)
222—Bag
222C—Bag Saddle
224—Valve
226—Mask
227—Mask Auxiliary Attachments
228—Mask Port
230—Mask Strap Assembly
232—Chin Strap
234—Quick Release
236—Mask Attachment
240—Forehead Strap Assembly
242—Forehead Strap
244—Forehead Bracket
246—Forehead Pad(s)
248—Mask Bridge
300—Emergency Respiratory Support System (3rd Embodiment)
320—Assisted Respiration Device
322—Bag
324—Valve
326—Endotracheal Tube
330—ET Bracket Assembly
332—ET Bracket
334—ET Insertion Cavity
336—ET Screw Support Cavity
338—ET Screw Head
340—ET Screw Threaded Portion
342—ET Screw Plate
344—Strap
346—Viewport
400—Emergency Respiratory Support System (4th Embodiment)
430—Assisted Respiration Device
432—Oxygen Supply Line
434—Oxygen Bag
436—Oxygen Mask
438—Coupler
440—Valve
442—Mask Attachment Strap
450—Forehead Strap
452—Forehead Pad
460—Mask Outlet(s)
462—Mask Inlet
470—Mask Auxiliary Strap
472—Auxiliary Strap Attachment Points
500—CPR Board
510—Patient Head Region
520—Holder Attachment Region

What is claimed is:

1. An emergency respiratory support system for providing respiratory support to a patient, the system comprising:

a base;

a plurality of blocks arranged on opposite sides of a head of the patient;

an assisted respiration device comprising a valve configured to provide ventilation and/or respiratory support to the patient and a bag configured to provide an air supply to the patient;

a holder assembly configured for attachment to the base and comprising a support rod extending from the base, a support arm rotatably mounted to the support rod, and a saddle coupled to the support arm and configured to support the bag of the assisted respiration device, wherein the saddle is movable along a length of the support arm to move the assisted respiration device to a position in proper alignment between the plurality of blocks relative to a position of a mouth and/or nose of the patient; and one or more straps configured for attachment, at a first end, to a first of the plurality of blocks and, at a second end, to a second of the plurality of blocks, and to secure the assisted respiration device to the patient.

2. The system of claim 1, wherein the air supply comprises a supplemental amount of oxygen from an external source, so an oxygen content of the air supply is elevated relative to an oxygen content of an ambient air source.

3. The system of claim 1, wherein the assisted respiration device comprises a bag valve mask device including a mask configured to cover the mouth and/or nose of the patient, and wherein the valve is configured to connect to an inlet of the mask.

4. The system of claim 3, wherein the holder assembly is configured to maintain a substantially air-tight seal around the patient's mouth, without requiring the mask to be held in place by a hand of a medical caregiver.

5. The system of claim 3, wherein the mask is secured to the plurality of blocks by at least one of the one or more straps.

6. The system of claim 5, wherein the one or more straps comprise a first strap, which is configured to secure the mask over the nose and mask of the patient and also to secure a lower portion of the head of the patient in place, and a second strap, which is connected to the mask and is secured to a forehead of the patient.

7. The system of claim 1, wherein the assisted respiration device comprises an endotracheal tube (ET) bracket that is configured to be secured to an endotracheal tube inserted in a trachea of the patient, and wherein the valve is configured to connect to an external end of the endotracheal tube.

8. The system of claim 1, wherein the bracket comprises a cushion configured to hold the bag.

9. The system of claim 1, comprising an oxygen mask configured to receive a supply of oxygen from an external oxygen source.

10. The system of claim 9, wherein the oxygen mask comprises a ring with a hook or loop fastener to secure the mask to a face of the patient using at least one of the one or more straps.

11. A method of providing emergency respiratory support to a patient, the method comprising:

securing the patient to a base, wherein a head of the patient is secured between a plurality of blocks arranged on opposite sides of the head of the patient;

providing an emergency respiratory support system comprising at least a valve and a bag;

securing the respiratory support system to a holder assembly attached to the base, wherein the holder assembly comprises a support rod extending from the base, a support arm rotatably mounted to the support rod, and a saddle coupled to the support arm and configured to support the bag of the assisted respiration device using one or more straps;

adjusting a position of the saddle along a length of the support arm such that the respiratory support system is arranged in proper alignment between the plurality of blocks relative to a position of a mouth and/or nose of the patient; and supplying respiratory support to the patient using the emergency respiratory support system.

12. The method of claim 11, wherein supplying respiratory support comprises supplying supplemental oxygen to the patient from an external oxygen source.

13. The method of claim 11, wherein the emergency respiratory support system comprises an endotracheal tube and/or a mask secured to the patient by the holder assembly.

14. The method of claim 13, wherein the mask is an oxygen mask.

15. The method of claim 11, wherein the plurality of blocks comprises a head immobilizer structure.

16. The method of claim 11, wherein supplying respiratory support to the patient is accomplished without manual intervention from a medical caregiver.

17. An emergency respiratory support system for providing respiratory support to a patient, the system comprising:

a base;

a plurality of blocks arranged on the base on opposite sides of a head of the patient;

an assisted respiration device comprising an oxygen bag configured to provide a supply of oxygen to the patient, an oxygen mask configured to cover a mouth and/or nose of the patient, and a valve configured to regulate a flow of the supply of oxygen between the oxygen bag and the oxygen mask;

a holder assembly attached to the base to secure the assisted respiration device relative to the patient and comprising a support rod extending from the base, a support arm rotatably mounted to the support rod, and a saddle coupled to the support arm and configured to support the oxygen bag of the assisted respiration device, wherein the saddle is movable along a length of the support arm to move the assisted respiration device to a position in proper alignment between the plurality of blocks relative to a position of a mouth and/or nose of the patient; and one or more straps configured for attachment, at a first end, to a first of the plurality of blocks and, at a second end, to a second of the plurality of blocks, and to secure the oxygen mask over the mouth and/or nose of the patient.

* * * * *